(12) United States Patent
Shivanandappa et al.

(10) Patent No.: US 7,045,648 B2
(45) Date of Patent: May 16, 2006

(54) COMPOUND AS CHOLINESTERASE INHIBITOR AND ITS ISOLATION FROM FUNGUS SPOROTRICHUM SPECIES

(75) Inventors: Thimmappa Shivanandappa, Karnataka (IN); Avinash Prahalad Sattur, Karnataka (IN); Shereen, Karnataka (IN); Soundar Divakar, Karnataka (IN); Nayakana Katte Ganesh Karanth, Karnataka (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/603,658

(22) Filed: Jun. 26, 2003

(65) Prior Publication Data

US 2004/0086987 A1    May 6, 2004

Related U.S. Application Data

(62) Division of application No. 10/107,806, filed on Mar. 28, 2002, now Pat. No. 6,759,552.

(51) Int. Cl.
*C07C 63/06*    (2006.01)

(52) U.S. Cl. .......................................... 560/8

(58) Field of Classification Search ................ 560/310, 560/8
See application file for complete search history.

(56) References Cited

FOREIGN PATENT DOCUMENTS

WO    WO 2003082794    * 10/2003

OTHER PUBLICATIONS

Harry Greenblatt et al Structural Studies on Vertebrate and Invertebrate Acetylcholineterase and their complexes with functional Ligands. 2000.*

* cited by examiner

*Primary Examiner*—Rita Desai
(74) *Attorney, Agent, or Firm*—Ann S. Hobbs; Venable LLP

(57) ABSTRACT

The present invention provides a novel bioactive compound 12-(2'-CARBOXY-5'-METHOXYPHENYL)-2,12-DIHYDROXY-DODECA-4-ONE "Sporotricolone", mainly as acetylcholinesterase (AchE) inhibitor, along with a process for the isolation of said compound from fungus *Sporotrichum* species.

1 Claim, No Drawings

COMPOUND AS CHOLINESTERASE INHIBITOR AND ITS ISOLATION FROM FUNGUS SPOROTRICHUM SPECIES

This application is a divisional of application Ser. No. 10/107,806, filed Mar. 28, 2002 now U.S. Pat. No. 6,759, 552.

FIELD OF INVENTION

The present invention relates to a compound 12-(2'-CARBOXY-5'-METHOXYPHENYL)-2,12-DIHYDROXY-DODECA-4-ONE "Sporotricolone", mainly as acetylcholinesterase (AchE) inhibitor. The present invention also relates to a process for the isolation of said compound from fungus *Sporotrichum* species.

BACKGROUND AND PRIOR ART REFERENCES

Enzyme inhibitors are important class of molecules that are used as drugs and pesticides. The enzyme acetylcholinesterase (AchE) is involved in the synaptic transmission of the nerve impulse and its inhibition leads to accumulation of the neurotransmitter, acetylcholine leading to overexcitation of the postsynaptic neuron. This property of the inhibitor has been exploited to develop newer insecticides against a wide range of insect pests as well as drugs effective against worms, and, recently a new class of neuroactive drugs against dementia (Alzheimer's).

Although earlier authors have isolated metabolites such asasteric acis, questin and questinol from *Sorortricum* sp., no AchE inhibitor activity has been reported(Slater, G P, Haskins, R H and Hogge, L. R. Can J Mirobiol 17 (1971), 1576–79). The fungi, *Aspergillus terreus* ( Ling, K H, Liou, H H, Yang, C M and Yang C K, Appl. Env. Microbiol, 37 (1979) 355–57) and *Penicillium* sp. (Omura, Skuno, F, Otoguro, K, Shiomi, K. Mauma, R and Iwai, Y. J. Antibiot. 48(1995) 745–46) have been reported to produce an AchE inhibitor named Arusigacin. However, the AchE inhibitor of the present invention is isolated from Sporotrichum having distinct chemical structure and properties and therefore a novel inhibitor molecule.

After screening of various microorganisms, a fungal culture is selected which shows inhibition against a serine esterase/protease/cholinesterase enzyme. This imperfect deuteromycetes, *Sporotrichum* species and was first isolated in 1966. The taxonomic features of *Sporotrichum* species (deuteromyces) are broad hyphae and septate in nature; has hyalline conidiophores with little differentiation from vegetatative hyphae and solitary conidia with broad attachment to the hyphae.

This culture has previously been a subject of research investigation at the Central Food Technological Research Institute (CFTRI) India, for its ability to grow on lignocellulosic wastes for the production of enzymes and organic acids (Sreekantaiah, K R, PhD thesis (1976) University of Mysore; Manonmani, H K, PhD thesis (1986) University of Mysore).

This culture has now been used in the present invention to produce a fermented extract containing a serine esterase/protease/cholinesterase inhibitor.

The conditions of fermentation have been described earlier in Indian Patent Application No. 303/DEL/2000 Sattur, A P, Shivanandappa, T, Divakar, S and Karanth, N G.

OBJECTS OF THE INVENTION

The main object of the present invention is to provide bioactive compound 12-(2'-CARBOXY-5'-METHOXYPHENYL)-2,12-DIHYDROXY-DODECA-4-ONE "Sporotricolone" having inhibitory activity against acetylcholinesterase (AchE).

Another object of the present invention is to provide a compound having inhibitory activity against serine esterase and protease.

Yet another object of the present invention is to provide a compound having insecticidal properties.

Still another object of the present invention is to provide a compound having enhanced cholinergic activity.

Yet another object of the present invention is to provide a process for the isolation of Sporotricolone.

SUMMARY OF THE INVENTION

The present invention provides a compound 12-(2'-CARBOXY-5'-METHOXYPHENYL)-2,12-DIHYDROXY-DODECA-4-ONE "Sporotricolone" mainly as acetylcholinesterase (AchE) inhibitor. The present invention also provides a process for the isolation of said compound from fungus *Sporotrichum* species.

DETAILED DESCRIPTION OF THE INVENTION

Accordingly, the present invention provides a bioactive compound 12-(2'-CARBOXY-5'-METHOXYPHENYL)-2, 12-DIHYDROXY-DODECA-4-ONE "Sporotricolone" of formula (I) having acetylcholinesterase (AchE) enzyme inhibition activity obtained from fungus *Sporotrichum* species.

FORMULA (I)

An embodiment of the present invention wherein the compound 12-(2'-CARBOXY-5'-METHOXYPHENYL)-2, 12-DIHYDROXY-DODECA-4ONE "Sporotricolone" of formula (I) having the following characteristic properties:

Solubility: Highly soluble in ethyl acetate, methanol and acetone.

UV (ethyl acetate) $\lambda_{max}$: 265 nm, 312 nm.

$^1$HNMR spectrum (DMSO, $\delta_{TMS=}$0.00 ppm); δ 1.03 (3H, d, J=6.3 Hz, —CH—$CH_3$) δ 1.2–2.7 (14H, m, 7×—$CH_2$) δ 3.6–3.8 (m, Ar—O—$CH_3$ and Ar—CH—OH) δ 7.20 (1H, d, J=2.5 Hz, $C_{6'}$—H) δ 7.30 (2H, d, J=7.1 Hz, $C_{3'}$—Hand $C_{4'}$—H)

Mass spectrum (EI, 70 eV, 25° C., 200-ul amp):

m/e: 336 (M+), 279(366–87), 167(274–112), 57 ($CH_2COCH_3$), 43, 29.

Another embodiment of the present invention, wherein the purity of the compound is established by TLC and RP HPLC.

Yet another embodiment of the present invention, wherein said compound is named as 12-(2'-CARBOXY-5'-METHOXYPHENYL)-2,12-DIHYDROXY-DODECA-4-ONE "Sporotricolone".

Still another embodiment of the present invention, wherein said compound is an inhibitor of the enzyme acetylcholinesterase from the rat brain as well as erythrocytes with a $IC_{50}$ value of $20 \times 10^{-6}$ M.

Yet another embodiment of the present invention, wherein said compound also acts as an inhibitor of serine esterase of the rat liver serum.

Still another embodiment of the present invention, wherein said compound having insecticidal properties.

Yet another embodiment of the present invention, wherein said compound effective against mosquito larvae at an optimum concentration of 70 μg/ml water (70 ppm) when exposed for 24 hrs.

Still another embodiment of the present invention, wherein the insecticidal activity of the compound against mosquito larvae is selected from *culex quinquifasciatus*.

Yet another embodiment of the present invention, wherein said compound as acetylcholineesterase inhibitor having potential application as a drug for Alzheimer's disease or dermentia.

The present invention also provides a process for the isolation of 12-(2'-CARBOXY-5'-METHOXYPHENYL)-2,12-DIHYDROXY-DODECA-4ONE Sporotricolone from the fungus *Sporotrichum* species, said process comprising the steps of:

(a) extracting the fermented solid with an organic solvent;
(b) filtering the extract of step (a) through a cloth or Whatman filter paper to obtain a clear solution;
(c) evaporating the solution of step (b) under reduced pressure to obtain a crude extract;
(d) purifying the crude extract of step (c) by column chromatography over silica gel and eluting with mixture of organic solvents of increasing polarity;
(e) pooling active eluted fraction of step (d) and further subjected to column chromatography over silica gel by eluting with mixture of organic solvents with increasing polarity;
(f) repooling the active eluted fractions of step (e);
(g) evaporating the pooled fractions of step (f) to get a residue; and
(h) dissolving the residue in step (g) in ethyl acetate to yield the pure compound "Sporotricolone".

Yet another embodiment of the present invention, a process wherein in step (a) the organic solvent is selected from a group consisting of ethyl acetate, acetone or methanol and preferably ethyl acetate.

Still another embodiment of the present invention, a process wherein in step (d) the mixture of organic solvents is selected from the combination of hexane:diethyl ether and chloroform: methanol mixtures.

Further embodiment of the present invention, a process wherein in step (e) the mixture of organic solvent used is chloroform: ethyl acetate mixture.

Yet another embodiment of the present invention, wherein the said compound is separated and purified by column chromatography on silica gel and RP HPLC.

Still another embodiment of the present invention, wherein said compound having an UV absorption at 265 and 312 nm.

The present invention is further explained in the form of following embodiments

In the present invention a process for the isolation of an acetylcholinesterase inhibitor, which comprises the extraction of the fermented broth culture with solvents such as ethyl acetate. The crude extract is further extracted with 10–20 ml of methanol and subjected to column chromatography using silica gel and eluted with various combinations of solvents such as hexane:diethyl ether (85:15, 50:50) followed by chloroform: methanol (95:5, 50:50, 10:90). Fractions are evaporated under nitrogen, dissolved in ethyl acetate and assayed for acetylcholinesterase (AchE) inhibition. The active fractions are pooled and further subjected to purification on silica gel column chromatography and eluted with chloroform: ethyl acetate (90:10, 50:50, 0:100). The active fractions pooled and the solvent evaporated and dissolved in 2 ml ethyl acetate. The purity, as checked by TLC, showed a single spot and HPLC on reverse phase column (C18) with chloroform and methanol as mobile phase. The yield is about 10 mg. The purified inhibitor showed inhibitor potency against rat brain AchE with an $IC_{50}$ of $15–20\times10^{-6}$ M.

A general process for the production of the novel Acetylcholinesterase inhibitor is given in the flow sheet:

Solid State Fermentation

Solvent extraction

Crude extract

Silica gel column chromatography I
(hexane, diethylether, chloroform & methanol)

enriched fraction

Silica gel column chromatography II
(Chloroform: ethyl acetate)

purified inhibitor
12-(2'-CARBOXY-5'-METHOXYPHENYL)-2,12-DIHYDROXY-DODECA-4-ONE "Sporotricolone"

The structure of the isolated inhibitor is determined by UV, $^1H$ NMR and mass spectrometry.

The following examples are given by way of illustration of the present invention and should not be construed to limit the scope of the invention.

EXAMPLE-1

The fermentation culture is extracted with 100 ml of ethyl acetate, filtered through a cotton filter and concentrated in vacuo to obtain 1 ml of the crude extract. This is used as a source of the enzyme inhibitor and 20 μl of the extract gave 60–90% inhibition of rat brain acetylcholinesterase enzyme.

EXAMPLE-2

The crude extract is further extracted with 10–20 ml of methanol and subjected to column chromatography using silica gel and eluted with various combinations of solvents such as hexane: diethyl ether (85:15, 50:50) followed by chloroform: methanol (95:5, 50:50, 10:90). Fractions are evaporated under nitrogen, dissolved in ethyl acetate and assayed for acetyl cholinesterase (AchE) inhibitor. The active fractions (#11–19) are pooled and further subjected to purification on silica gel column chromatography and eluted with chloroform: ethyl acetate (90:10, 50:50, 0:100). The active fractions pooled and the solvent evaporated and dissolved in 2 ml ethyl acetate. The purity, as checked by TLC, showed a single spot. RP HPLC also ascertained the purity on a C18 column with chloroform and methanol as the mobile phase wherein it is a single peak. The yield is about 10 mg.

EXAMPLE-3

The purified inhibitor showed inhibitor potency against rat brain AchE with an IC50 of $15-20 \times 10^{-6}$ M, as assayed according to Ellman et al., (Biochem. Pharmacol. 7(1961), 88–95) and is given as follows: The enzyme inhibition is carried out by pre-incubating the enzyme (rat brain acetylcholinesterase) with 2–20 ul of the culture extract or the column fraction at room temperature (25° C.) for 15 minutes followed by the addition of the substrate, acetyl thiocholine iodide (0.5 mM), in 3 ml phosphate buffer (0.1. M, pH.7.4) containing 0.25 mM dithiobisnitrobenzoic acid. Absorbance change at 412 nm is monitored every 30 seconds for 2 min in an UV-VIS Spectrophotometer. Inhibition is calculated relative to the solvent control. $IC_{50}$ is determined by regression analysis.

ADVANTAGES

1. The present invention provides an AchE /serine esterase/ protease inhibitor from a microbial source.
2. The present invention provides a simple extraction and chromatographic procedure to purify the AchE inhibitor from the crude mixture.
3. In the present invention the isolated inhibitor is a novel bioactive molecule

The invention claimed is:

1. A method of inhibiting acetylcholinesterase in a subject wherein the subject is a human afflicted with Alzheimer's Disease comprising administering to the subject an effective amount of a compound of the formula:

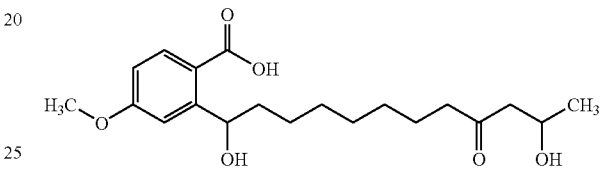

* * * * *